(12) United States Patent
Fu et al.

(10) Patent No.: US 10,925,968 B2
(45) Date of Patent: Feb. 23, 2021

(54) CELL INTERNALIZING COMPOUNDS

(71) Applicant: Sorrento Therapeutics, Inc., San Diego, CA (US)

(72) Inventors: Yanwen Fu, San Diego, CA (US); Gunnar F. Kaufmann, San Diego, CA (US); Heehyoung Lee, Arcadia, CA (US); Tong Zhu, San Diego, CA (US); Henry Hongjun Ji, Rancho Santa Fe, CA (US)

(73) Assignee: Sorrento Therapeutics, Inc., San Diego, CA (US)

( * ) Notice: Subject to any disclaimer, the term of this patent is extended or adjusted under 35 U.S.C. 154(b) by 0 days.

(21) Appl. No.: 16/455,184

(22) Filed: Jun. 27, 2019

(65) Prior Publication Data

US 2019/0358336 A1    Nov. 28, 2019

Related U.S. Application Data

(63) Continuation of application No. PCT/IB2018/050052, filed on Jan. 4, 2018.

(60) Provisional application No. 62/442,391, filed on Jan. 4, 2017, provisional application No. 62/556,813, filed on Sep. 11, 2017.

(51) Int. Cl.
| | | |
|---|---|---|
| *A61K 47/58* | (2017.01) | |
| *A61K 47/59* | (2017.01) | |
| *A61K 31/365* | (2006.01) | |
| *C07K 16/18* | (2006.01) | |

(52) U.S. Cl.
CPC .......... *A61K 47/605* (2017.08); *A61K 31/365* (2013.01); *A61K 47/595* (2017.08); *C07K 16/18* (2013.01)

(58) Field of Classification Search
None
See application file for complete search history.

(56) References Cited

FOREIGN PATENT DOCUMENTS

| WO | 2010006237 | 1/2010 | | |
|---|---|---|---|---|
| WO | 2015031837 | 3/2015 | | |
| WO | WO 2015/031837 A2 * | 3/2015 | ............. | A61K 38/14 |

OTHER PUBLICATIONS

Farooqui et al. "Effect of structural variations in cholesteryl-conjugated oligonucleotides on inhibitory activity toward HIV-1" Bioconjugate Chem. vol. 2, No. 6. pp. 422-426. (Year: 1991).*
International Search Report and Written Opinion issued in corresponding PCT Application No. PCT/IB2018/050052, dated Jul. 6, 2018, 21 pages.
Antopolsky M et al, "Peptide-Oligonucleotide Phosphorothioate Conjugates With Membrane Translocation and Nuclear Localization Properties", Bioconjugate Chemistry, American Chemical Society, US,vol. 10, No. 4, Jan. 1, 1999 (Jan. 1, 1999), p. 598-606.
Torres Adrian G et al, "Exploiting cell surface thiols to enhance cellular uptake", Trends in Biotechnology,vol. 30, No. 4, Jan. 1, 2012 (Jan. 1, 2012), p. 185-190.
A. G. Torres et al, "Chemical structure requirements and cellular targeting of microRNA-122 by peptide nucleic acids anti-miRs", Nucleic Acids Research,vol. 40, No. 5, Nov. 8, 2011 (Nov. 8, 2011), p. 2152-2167.
Soline Aubry et al, "Cell-surface thiols affect cell entry of disulfide-conjugated peptides", The FASEB Journal, vol. 23, No. 9, Sep. 1, 2009 (Sep. 1, 2009), p. 2956-2967.
Saito Go et al, "Drug delivery strategy utilizing conjugation via reversible disulfide linkages: Role and site of cellular reducing activities", Advanced Drug Delivery Reviews, Elsevier, Amsterdam, NL,vol. 55, No. 2, Feb. 10, 2003 (Feb. 10, 2003), p. 199-215.

* cited by examiner

*Primary Examiner* — Joseph R Kosack
(74) *Attorney, Agent, or Firm* — McNeill Baur PLLC

(57) ABSTRACT

Provided herein are cell penetrating compounds having the Formula I:

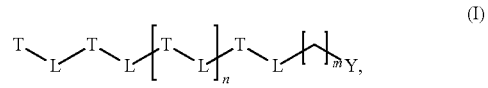

where, generally, each T is a thiol reactive group (e.g., a phosphorothioate), each L is a linker (e.g., a linear alkyl), and Y is a biologic (e.g., an antibody). Also provided are pharmaceutical compositions including the cell penetrating compounds, and methods of delivering the compound into a cell.

17 Claims, 3 Drawing Sheets

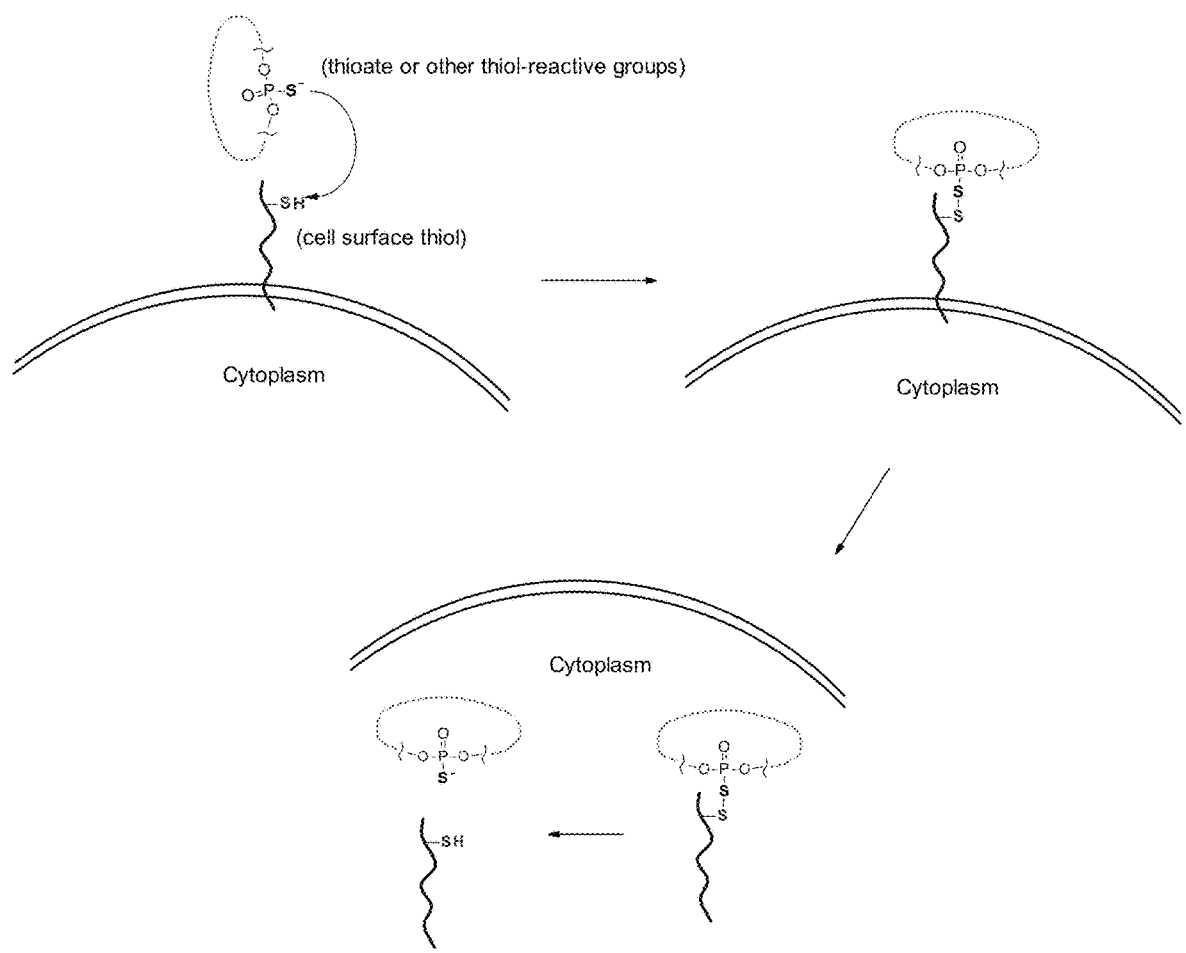
FIG 1. Proposed mechanism of cellular uptake of thiol-specific moieties through cell surface thiols.

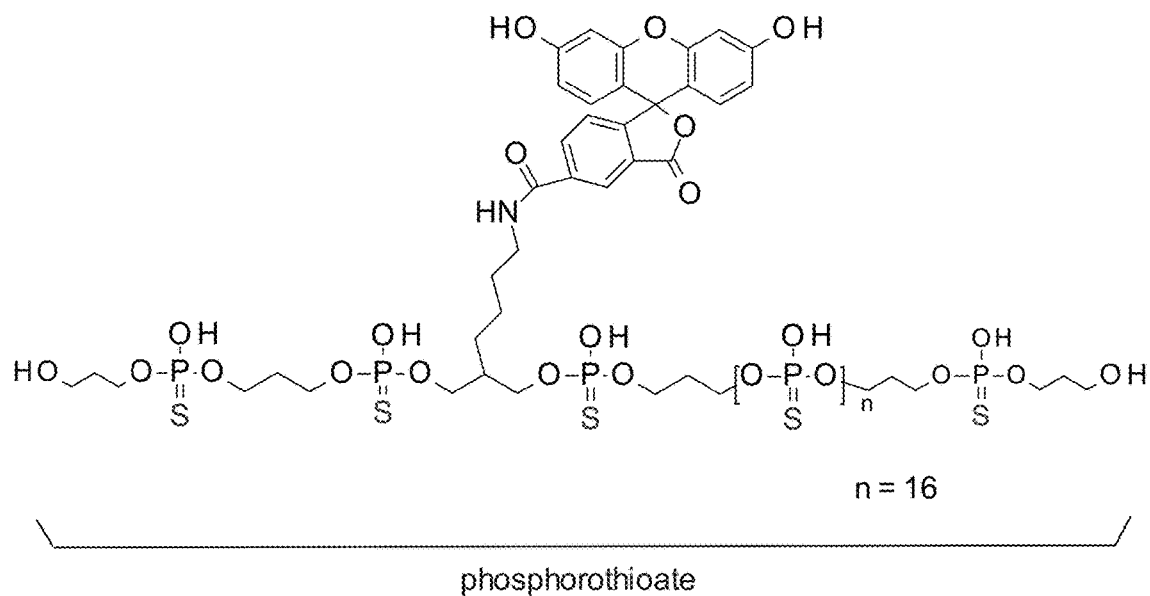
FIG 2. Structure of a phosphorothioate - fluorescein compound.
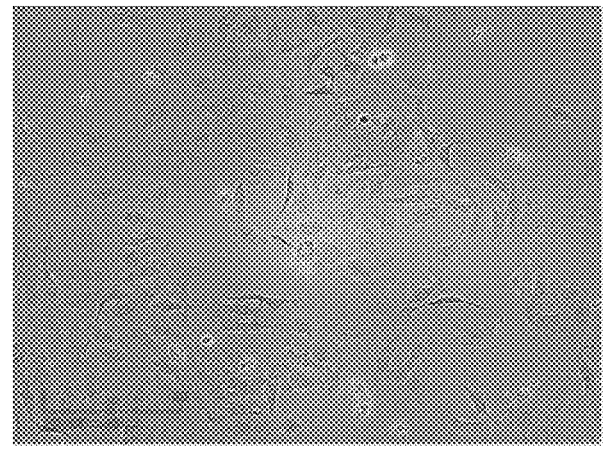
FIG 3. Cellular uptake of the phosphorothioate-fluorescein compound.

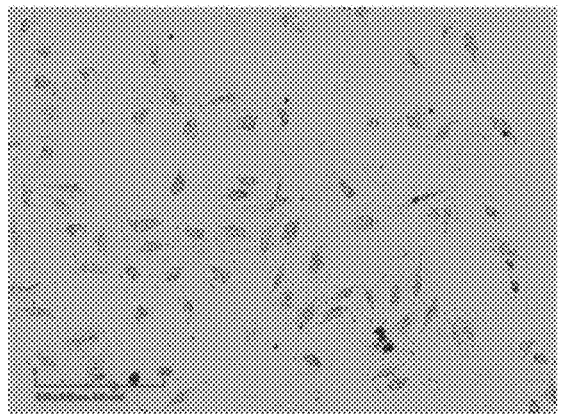
FIG 4. Cellular uptake of a cell internalizing anti-Stat3 antibody phosphorothioate compound.

CELL INTERNALIZING COMPOUNDS

RELATED APPLICATIONS

This application is a continuation application of PCT Application No. PCT/IB2018/050052, filed Jan. 4, 2018, which claims priority to U.S. provisional patent application No. 62/442,391, filed Jan. 4, 2017 and U.S. provisional patent application No. 62/556,813, filed Sep. 11, 2017, each of which is incorporated by reference herein in its entirety.

FIELD

The invention generally relates to novel cell internalizing compounds.

BACKGROUND

Membrane proteins, such as transmembrane proteins, surface-linked proteins, and proteins non-covalently bound to the cellular surface, present exposed thiol groups in reduced (—SH) or oxidized (S—S) form. And thiolation of biomolecules has been proposed to enhance cellular association and internalization. Torres, Adrian G and Gait, Michael J., Exploiting cell surface thiols to enhance cellular uptake. Trends in Biotechnology 30:185-190 (April 2012).

This application provides a novel cell internalizing compound as a vehicle to translocate biologic agents across the cell membrane.

SUMMARY

It has now been found that the novel cell internalizing compounds described herein, and pharmaceutically acceptable compositions thereof, effectively deliver a biologic agent intracellularly. Such compounds include those having the Formula I:

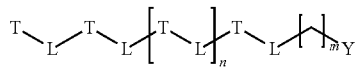

wherein, generally each of T is a thiol reactive moiety (e.g., phosphorothioate), each L is a linker, n and m are as defined herein, and Y is a biomolecule (e.g., an antibody, protein or nucleic acid).

BRIEF DESCRIPTION OF THE FIGURES

FIG. 1 depicts a proposed mechanism of cellular uptake through cell surface thiols.

FIG. 2 depicts the structure of the cell internalizing fluorescein compound.

FIG. 3 depicts the cellular uptake of the cell internalizing fluorescein compound depicted in FIG. 2.

FIG. 4 depicts the cellular uptake of a cell internalizing compound that includes an anti-STAT3 antibody.

DETAILED DESCRIPTION

1. General Description of Compounds

In certain embodiments, the present disclosure provides a compound of Formula I:

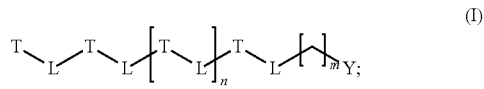

or a pharmaceutically acceptable salt thereof, wherein
each T is independently selected from a thiol reactive group, phosphorothioate, a thiophospho amino acid and maleimide;
each L is a linker group; and
Y is a protein, an antibody, a peptide, or a nucleic acid; and
n is an integer from 1 to 50; and
m is 0, 1, or 2.

2. Definitions

In order that the disclosure may be more readily understood, certain terms are first defined. These definitions should be read in light of the remainder of the disclosure and as understood by a person of ordinary skill in the art. Unless defined otherwise, all technical and scientific terms used herein have the same meaning as commonly understood by a person of ordinary skill in the art. Additional definitions are set forth throughout the detailed description An "antigen binding protein" is a protein comprising a portion that binds to an antigen and, optionally, a scaffold or framework portion that allows the antigen binding portion to adopt a conformation that promotes binding of the antigen binding protein to the antigen. Examples of antigen binding proteins include antibodies, antibody fragments (i.e., an antigen binding portion of an antibody), antibody derivatives, and antibody analogs. The antigen binding protein can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the antigen binding protein as well as wholly synthetic scaffolds comprising, for example, a biocompatible polymer. See, for example, Korndorfer et al., 2003, Proteins: Structure, Function, and Bioinformatics, Volume 53, Issue 1:121-129; Roque et al., 2004, Biotechnol. Prog. 20:639-654. In addition, peptide antibody mimetics ("PAMs") can be used, as well as scaffolds based on antibody mimetics utilizing fibronection components as a scaffold.

The term "antibody" refers to an immunoglobulin (Ig) molecule comprised of four polypeptide chains, two heavy (H) chains and two light (L) chains, or any functional fragment, mutant, variant, or derivation thereof, which retains the essential epitope binding features of an Ig molecule.

An "antibody fragment", "antibody portion", "antigen-binding fragment of an antibody", or "antigen-binding portion of an antibody" refers to a molecule other than an intact antibody that comprises a portion of an intact antibody that binds the antigen to which the intact antibody binds. Examples of antibody fragments include, but are not limited to, Fv, Fab, Fab', Fab'-SH, F(ab')2; Fd; and Fv fragments, as well as dAb; diabodies; linear antibodies; single-chain antibody molecules (e.g. scFv); polypeptides that contain at least a portion of an antibody that is sufficient to confer specific antigen binding to the polypeptide. Antigen binding portions of an antibody may be produced by recombinant DNA techniques or by enzymatic or chemical cleavage of intact antibodies. Antigen binding portions include, inter alia, Fab, Fab', F(ab')2, Fv, domain antibodies (dAbs), and complementarity determining region (CDR) fragments, chimeric antibodies, diabodies, triabodies, tetrabodies, and the like.

The term "human antibody", as used herein, refers to recombinant antibodies having one or more variable and constant regions derived from human immunoglobulin sequences. In one embodiment, all of the variable and constant domains are derived from human immunoglobulin sequences (a fully human antibody). These antibodies may be prepared in a variety of ways, examples of which are described below, including through the immunization with an antigen of interest of a mouse that is genetically modified to express antibodies derived from human heavy and/or light chain-encoding genes.

The term "alkyl" used alone, or as part of a larger moiety, means saturated straight-chain or branched monovalent hydrocarbon radical. The term "$(C_1-C_6)$alkyl" means a radical having from 1 to 6 carbon atoms in a linear or branched arrangement. And, generally, the term "(C#-C#)" means a radical having the range of carbon atoms indicated.

The term "carbocyclyl" as used herein, means a monocyclic, bicyclic (e.g., a bridged or spiro bicyclic ring), polycyclic (e.g., tricyclic or more), or fused hydrocarbon ring system that is completely saturated or that contains one or more units of partial unsaturation, but where there is no aromatic ring. A "cycloalkyl" is a completely saturated carbocycle. Monocyclic carbocyclyl groups include, without limitation, cyclopropyl, cyclobutyl, cyclopentyl, cyclopentenyl, cyclohexyl, cyclohexenyl, cycloheptyl, cycloheptenyl, and cyclooctyl.

An "cell internalizing compound", as used herein, refers to a compound that includes a cell internalizing moiety conjugated (covalently or non-covalently) to a biologic (e.g., an antibody or antibody fragment) which is capable of internalizing into a cell. Examples of intracellular delivery compounds (conjugated to an antibody) are provided throughout this specification.

The terms "polynucleotide," "oligonucleotide" and "nucleic acid" are used interchangeably throughout and include DNA molecules (e.g., cDNA or genomic DNA), RNA molecules (e.g., mRNA), analogs of the DNA or RNA generated using nucleotide analogs (e.g., peptide nucleic acids and non-naturally occurring nucleotide analogs), and hybrids thereof. The nucleic acid molecule can be single-stranded or double-stranded. In one embodiment, the nucleic acid molecules of the invention comprise a contiguous open reading frame encoding an antibody, or a fragment, derivative, mutein, or variant thereof.

Pharmaceutically acceptable salts of the compounds herein are contemplated. For use in medicines, the salts of the compounds described herein refer to non-toxic "pharmaceutically acceptable salts." Pharmaceutically acceptable salt forms include pharmaceutically acceptable acidic/anionic or basic/cationic salts.

The term "pharmaceutically acceptable carrier" refers to a non-toxic carrier, adjuvant, or vehicle that does not destroy the pharmacological activity of the compound with which it is formulated. Pharmaceutically acceptable carriers, adjuvants or vehicles that may be used in the compositions of this disclosure include, but are not limited to, organic or inorganic carriers, excipients or diluents suitable for pharmaceutical applications.

As used herein the terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed, i.e., therapeutic treatment. In other embodiments, treatment may be administered in the absence of symptoms. For example, treatment may be administered to a susceptible individual prior to the onset of symptoms (e.g., in light of a history of symptoms and/or in light of genetic or other susceptibility factors), i.e., prophylactic treatment. Treatment may also be continued after symptoms have resolved, for example to prevent or delay their recurrence.

The term "effective amount" as used herein, refers to an amount of a compound disclosed herein, which is sufficient to effect treatment of a disease when administered to a subject. A therapeutically effective amount will vary depending upon the relative activity of the compound and depending upon the subject and disease condition being treated, the weight and age of the subject, the severity of the disease condition, the manner of administration and the like, which can readily be determined by one of ordinary skill in the art.

3. Description of Exemplary Compounds

In a first embodiment, the present disclosure provides a compound of Formula I:

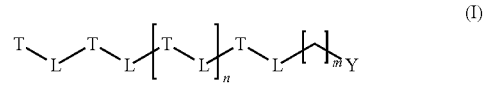

(I)

or a pharmaceutically acceptable salt thereof, wherein each T is selected from a thiol reactive group, phosphorothioate, a thiophospho amino acid and maleimide; each L is a linker group; Y is a protein, an antibody, a peptide, or a nucleic acid; n is an integer from 1 to 50; and m is 0, 1, or 2. Where m is 0, Y bonds directly to an L.

In a second embodiment, each L in Formula I is independently selected from a polyethylene glycol (PEG), an alkyl or a cyclic alkyl, wherein the remaining variables are as described above for Formula I.

In a third embodiment, n in Formula I is an integer from 5 to 25, wherein the remaining variables are as described above for Formula I. In another embodiment n is 15, 16 or 17, wherein the remaining variables are as described above for Formula I.

In another embodiment, each T in Formula I is independently selected from:

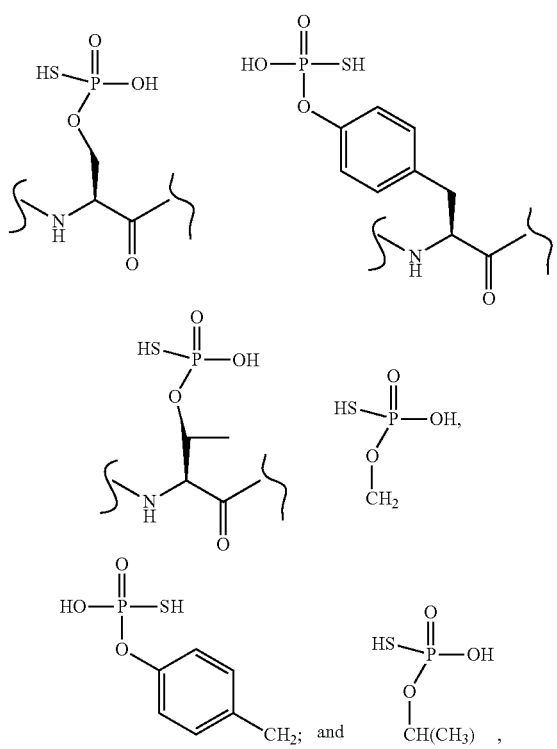

wherein the remaining variables are as described above for Formula I.

In further embodiments, each L in Formula I is independently selected from a polyethylene glycol (PEG), a linear alkyl, and a cyclic alkyl; or each L is a linear ($C_1$-$C_6$)alkyl, or a cyclic alkyl; or each L is a linear ($C_2$-$C_4$)alkyl, or ($C_5$-$C_{10}$)cyclic alkyl; or each L is a linear propyl alkyl, wherein the remaining variables are as described above for Formula I.

The present disclosure also provides a compound of Formula II:

is —(O—$CH_2$—$CH_2$)$_p$—, wherein p is an integer from 1 to 5, wherein the remaining variables are as described above for Formula II.

In another embodiment, each each R is H, each L is —$CH_2$—, n is 15, 16 or 17, and Y is an antibody in Formula II. In yet another embodiment, n is 16 in Formula II.

The present disclosure also provides a compound of Formula III:

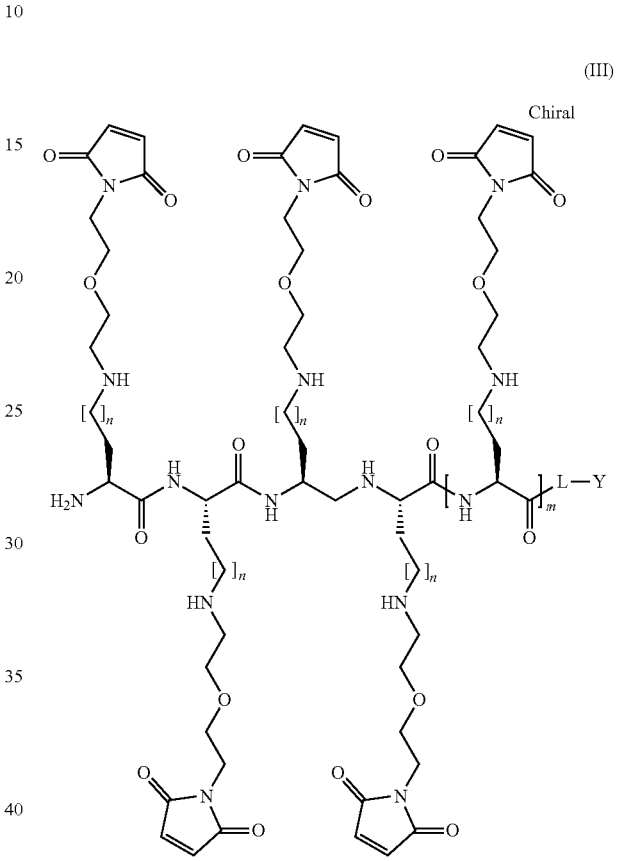

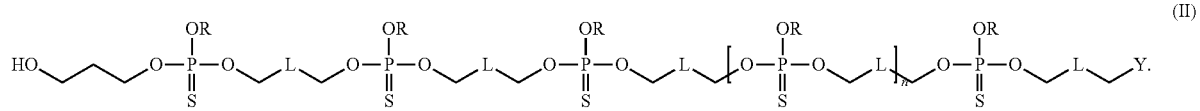

or a pharmaceutically acceptable salt thereof, wherein: each R is $CH_3$ or H; each L is a linker; Y is a protein, an antibody, a peptide, or a nucleic acid; and n is an integer from 5 to 25.

In other embodiments, n in Formula II is an integer from 12 to 20, or n is 15, 16 or 17, wherein the remaining variables are as described above for Formula II.

In other embodiments, each L in Formula II is independently selected from a polyethylene glycol (PEG), a linear alkyl, and a cyclic alkyl; or each L is a linear alkyl; or each L is independently selected from a linear ($C_2$-$C_6$)alkyl, or a cyclic ($C_5$-$C_6$)alkyl, and —(O—$CH_2$—$CH_2$)$_p$—, wherein p is an integer from 1 to 5; or each L is —$CH_2$—; or each L or a pharmaceutically acceptable salt thereof, wherein: L is a linker; n is an integer from 1 to 3; m is an integer from 5 to 25; and Y is a protein, an antibody, a peptide, or a nucleic acid.

In other embodiments, variable m in Formula III is an integer from 15 to 20, or m is 16, 17 or 18, wherein the remaining variables are as described above for Formula III.

In other embodiments, L in Formula III is a PEG, a linear alkyl, or a cyclic alkyl; or L is a linear ($C_2$-$C_{10}$)alkyl, and —(O—$CH_2$—$CH_2$)$_p$—, wherein p is an integer from 1 to 5, wherein the remaining variables are as described above for Formula III The present disclosure also provides a compound of Formula IV:

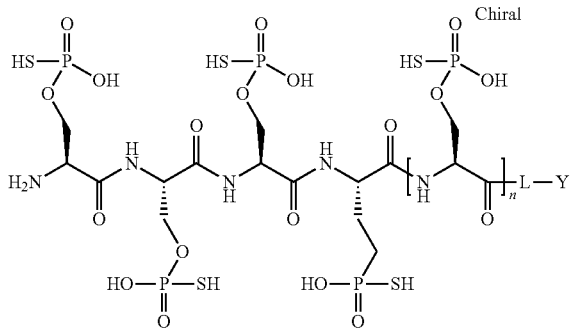

or a pharmaceutically acceptable salt thereof, wherein: L is a linker group; Y is a protein, an antibody, a peptide, or a nucleic acid; and n is an integer from 5 to 25

In additional embodiments, variable n in Formula IV is an integer from 15 to 20, or n is 16, 17 or 18, wherein the remaining variables are as described above for Formula IV.

In additional embodiments, L in Formula IV is a PEG, a linear alkyl, or a cyclic alkyl; or L is a linear $(C_2$-$C_{10})$alkyl, a $(C_5$-$C_6)$cyclic alkyl, or —(O—CH$_2$—CH$_2$)$_p$—, wherein p is an integer from 1 to 5; or L is a linear $(C_3$-$C_6)$alkyl, wherein the remaining variables are as described above for Formula IV.

The present disclosure also provides a compound of Formula V:

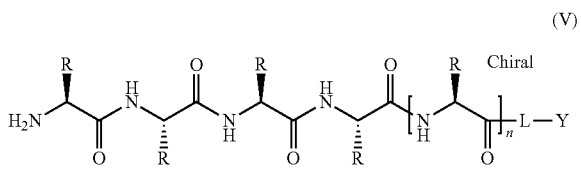

or a pharmaceutically acceptable salt thereof, wherein: L is a linker; Y is a protein, an antibody, a peptide, or a nucleic acid; n is an integer from 5 to 25; and each R is independently selected from the group consisting of:

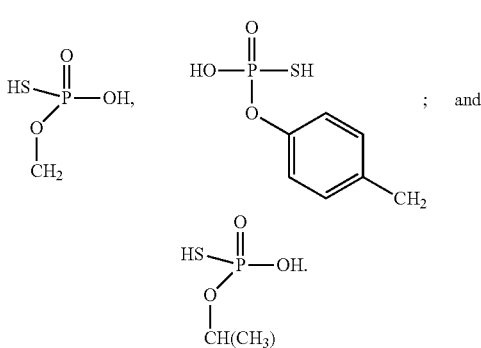

In additional embodiments, variable n in Formula V is an integer from 15 to 20, or n is 16, 17 or 18, wherein the remaining variables are as described above for Formula V.

In additional embodiments, L in Formula V is a PEG, a linear alkyl, or a cyclic alkyl; or L is a linear $(C_2$-$C_{10})$alkyl, a cyclic $(C_5$-$C_6)$alkyl, or —(O—CH$_2$—CH$_2$)$_p$—, wherein p is an integer from 1 to 5; or L is a linear $(C_3$-$C_6)$alkyl, wherein the remaining variables are as described above for Formula V.

In additional embodiments, Y in any of Formulae I-V is an antibody or antibody fragment, wherein the remaining variables are as described above.

In additional embodiments, Y in any of Formulae I-V is a human antibody or human antibody fragment, wherein the remaining variables are as described above.

In additional embodiments, Y in any of Formulae I-V is an antigen binding protein, wherein the remaining variables are as described above.

In additional embodiments, Y in any of Formulae I-V is peptide, wherein the remaining variables are as described above.

In additional embodiments, Y in any of Formulae I-V is protein, wherein the remaining variables are as described above.

In additional embodiments, Y in any of Formulae I-V is nucleic acid, wherein the remaining variables are as described above.

Specific examples of compounds are provided throughout the disclosure. Pharmaceutically acceptable salts as well as the neutral forms of these compounds are included herein.

4. Uses, Formulation and Administration

The compounds described herein may be used as a vehicle to carry biomolecules (e.g., proteins, peptides, nucleic acids) into cells to target previously "undruggable" targets. The carrier compounds described herein contain thiol-specific or thiol-reactive moieties, such as phosphorothioate, maleimide, or thiols, etc. Without wishing to be bound to any particularly theory, it is believed that the disclosed novel compounds react with cell surface thiols under physiological conditions to form a transitional covalent bond and trigger or facilitate a cellular uptake process (FIG. 1). The thiol-specific groups can be conjugated to biologics of interests, such as therapeutics or diagnostic agents, through chemical methods or biology approaches. The biologic containing compounds have been founds to translocate across cell membrane and reach intracellular targets.

In certain embodiments, the present disclosure provides compounds useful for treating a subject (e.g., a human) with a disease or disorder defined herein comprising the step of administering to the patient an effective amount of a compound of Formula I, or a pharmaceutically acceptable salt or composition thereof.

The amount of a provided compound that may be combined with carrier materials to produce a composition in a single dosage form will vary depending upon the patient to be treated and the particular mode of administration.

Compounds or compositions described herein may be administered using any amount and any route of administration effective for treating or lessening the severity of one or more of the diseases and conditions described herein. A specific dosage and treatment regimen for any particular patient will depend upon a variety of factors, including age, body weight, general health, sex, diet, time of administration, rate of excretion, drug combination, the judgment of the treating physician, and the severity of the particular disease being treated.

Compounds and compositions described herein are useful for intracellular delivery of, or to enhance the intracellular delivery of, one or more biologics, including antigen binding proteins (e.g., antibodies and antibody fragments), proteins, peptides and nucleic acids. Thus, it will be appreciated that the present disclosure provides a method of treating a disease or disorder that could be treated by, for example, an anti-STAT3 antibody.

In certain embodiments, the compounds and compositions described herein are useful in treating cancer or other neoplastic condition in a subject in need thereof. In certain embodiments, the compounds and compositions described herein are useful in treating infections in a subject in need thereof. In certain embodiments, the compounds and compositions described herein are useful in treating neurological conditions or disorders in a subject in need thereof.

In another aspect, a diagnostic compound or imaging compound is provided. The compound is any compound defined by the formulas above, except that Y is a diagnostic agent or imaging agent. And also provided is a method of delivering a diagnostic agent or imaging agent to cell target. The method includes administering a diagnostic compound or the imaging compound defined by the formulas above, except that Y is a diagnostic agent or imaging agent to a cell target, for example, by delivering to cells in vitro or by administering to a subject an effective amount of the compound.

EXEMPLIFICATION

As depicted in the Examples below, in certain exemplary embodiments, compounds are prepared according to the following general procedures. It will be appreciated that, although the general methods depict the synthesis of certain compounds herein, the following general methods, and other methods known to one of ordinary skill in the art, can be applied to all compounds described herein.

Cell Internalization of Fluorescein-Phosphorothioate 20 Mer Compound

To confirm cell internalization, the following phosphorothioate 20 mer was synthesized:

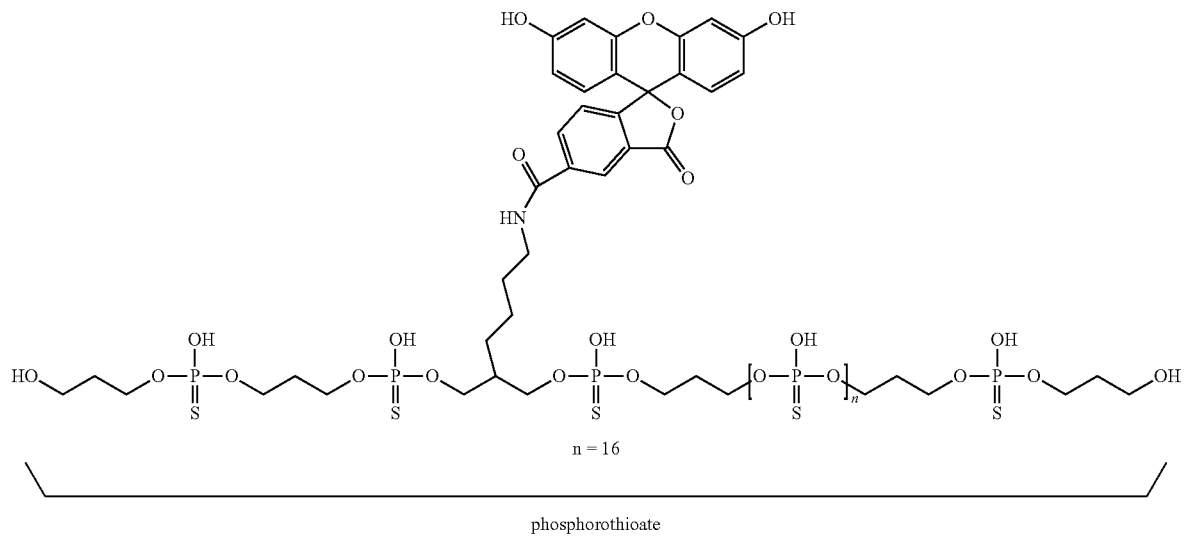

Cell internalization of this compound was tested at 10 uM in HUVEC. Cells (HUVEC and HELA) were plated overnight in their culture media (5K/well, 96 wp). The day of the experiment, media is replaced with Fluorobrite (no serum).

Then, the compounds were prepared in Fluorobrite and distributed to cells, to a final 10 uM in duplicate. After 60 min incubation SN is aspirated and replaced with fresh media, to allow for visualization on Incucyte. The results are depicted in FIG. 3.

Detection of Conjugate Internalization (2H Incubation) with PE-Anti-Human IgG

To confirm internalization of an antibody, a STAT3 antibody was conjugated to the phosphorothioate 20 mer:

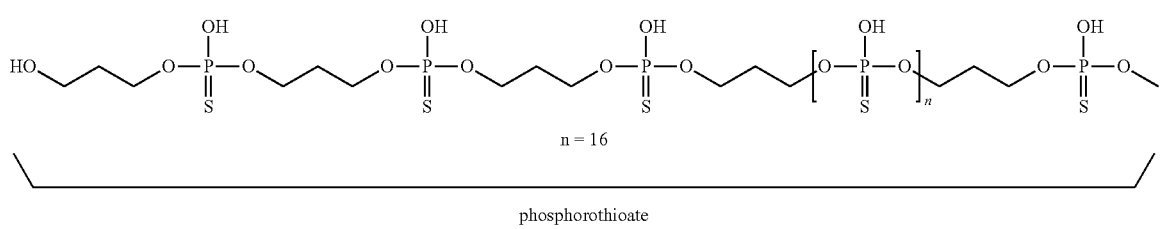

Cell internalization was tested and the results are depicted in FIG. 4.

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

What is claimed is:

1. A compound having the Formula II:

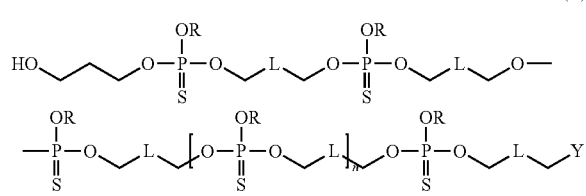

or a pharmaceutically acceptable salt thereof, wherein:
each R is $CH_3$ or H;
each L is independently a polyethylene glycol (PEG), a linear alkyl, or a cyclic alkyl;
Y is a protein, an antibody, a peptide, or a nucleic acid; and
n is an integer from 5 to 25.

2. The compound of claim 1, wherein n is an integer from 12 to 20.

3. The compound of claim 1, wherein n is 15, 16 or 17.

4. The compound claim 1, wherein each L is a linear alkyl.

5. The compound of claim 1, wherein each L is independently a linear $(C_2\text{-}C_6)$alkyl, or a cyclic $(C_5\text{-}C_6)$alkyl, or $-(O-CH_2-CH_2)_p-$, wherein p is an integer from 1 to 5.

6. The compound of claim 1, wherein each L is $-CH_2-$.

7. The compound of claim 1, wherein each L is $-(O-CH_2-CH_2)_p-$, wherein p is an integer from 1 to 5.

8. The compound of claim 1, wherein each R is H, each L is $-CH_2-$, n is 15, 16 or 17, and Y is an antibody.

9. The compound of claim 8, wherein n is 16.

10. The compound of claim 1, wherein Y is an antibody or antibody fragment.

11. The compound of claim 1, wherein Y is a peptide.

12. The compound of claim 1, wherein Y is a protein.

13. The compound of claim 1, wherein Y is a nucleic acid.

14. A pharmaceutical composition comprising the compound of claim 1, or a pharmaceutically acceptable salt thereof; and a pharmaceutically acceptable carrier.

15. A method of delivering a therapeutic agent into a cell comprising contacting a cell with a compound of claim 1 or a pharmaceutical composition comprising the compound or a pharmaceutically acceptable salt thereof and a pharmaceutically acceptable carrier, wherein the compound is internalized into the cell.

16. A pharmaceutical composition comprising the compound of claim 12, or a pharmaceutically acceptable salt thereof; and a pharmaceutically acceptable carrier.

17. A method of delivering a therapeutic agent into a cell comprising contacting a cell with a compound of claim 1 or a pharmaceutical composition comprising the compound or a pharmaceutically acceptable salt thereof and a pharmaceutically acceptable carrier, wherein the compound is internalized into the cell.

* * * * *